United States Patent [19]

Neubauer et al.

[11] Patent Number: 5,032,684

[45] Date of Patent: Jul. 16, 1991

[54] CONTINUOUS PURIFICATION OF CAPROLACTAM

[75] Inventors: Gerald Neubauer, Weinheim; Josef Ritz; Hugo Fuchs, both of Ludwigshafen; David Agar, Rimbach; Rolf Fischer, Heidelberg; Uwe Vagt, Speyer, all of Fed. Rep. of Germany

[73] Assignee: BASF Aktiengesellschaft, Ludwigshafen, Fed. Rep. of Germany

[21] Appl. No.: 551,790

[22] Filed: Jul. 12, 1990

[30] Foreign Application Priority Data

Aug. 2, 1989 [DE] Fed. Rep. of Germany ....... 3925575

[51] Int. Cl.$^5$ ............................................. C07D 201/16
[52] U.S. Cl. ................................................... 540/540
[58] Field of Search ........................................ 540/540

[56] References Cited

U.S. PATENT DOCUMENTS 2,786,052  3/1957  Kampschmidt ................... 540/540

FOREIGN PATENT DOCUMENTS

| | | | |
|---|---|---|---|
| 0138241 | 4/1985 | European Pat. Off. ............ | 540/540 |
| 898000 | 11/1953 | Fed. Rep. of Germany ....... | 540/540 |
| 1253715 | 9/1969 | Fed. Rep. of Germany ...... | 540/540 |
| 1253716 | 9/1969 | Fed. Rep. of Germany ...... | 540/540 |
| 1470365 | 10/1974 | Fed. Rep. of Germany ...... | 540/540 |
| 2508247 | 9/1976 | Fed. Rep. of Germany ...... | 540/526 |
| 1004616 | 3/1987 | Fed. Rep. of Germany ...... | 540/540 |
| 75083 | 8/1970 | German Democratic Rep. .................................. | 540/540 |
| 969993 | 9/1962 | United Kingdom ................ | 540/540 |
| 908859 | 10/1962 | United Kingdom ................ | 540/540 |
| 1002424 | 8/1965 | United Kingdom ................ | 540/540 |
| 1528513 | 10/1978 | United Kingdom ................ | 540/536 |

*Primary Examiner*—Robert T. Bond
*Attorney, Agent, or Firm*—Keil & Weinkauf

[57] ABSTRACT

Caprolactam is purified continuously by passing a 75–95% strength by weight aqueous caprolactam solution together with hydrogen at 50–95° C. and 1.5–100 bar upward through a fixed-bed supported palladium or nickel catalyst in a tubular zone while maintaining a residence time of from 10 to 100 min.

7 Claims, No Drawings

CONTINUOUS PURIFICATION OF CAPROLACTAM

Caprolactam as a fiber raw material must increasingly meet higher purity requirements. This requires that certain parameters of the caprolactam, including the permanganate number and the volatile bases content, be minimized.

DE patent U.S. Pat. No. 1,253,716 discloses a process wherein caprolactam is hydrogenated in the presence of hydrogenation catalysts in suspension or in a trickle bed by the addition of acids such as sulfuric acid. In a similar process described in DE patent U.S. Pat No. 1,253,715, the hydrogenation is carried out in the presence of an alkali. This has the disadvantage that both the acid and the alkali need to be removed again from the hydrogenated caprolactam.

In another process, described in DE patent U.S. Pat. No. 1,004,616, impure caprolactam is treated first with activated carbon and then with an ion exchanger and thereafter hydrogenated in suspension or in a trickle bed in the presence of hydrogenation catalysts and the hydrogenated caprolactam is then treated with an ion exchanger. Furthermore, DD patent U.S. Pat No. 75,083 discloses a process for purifying caprolactam by first distilling caprolactam, then hydrogenating the caprolactam in solution in an organic solvent or water in the presence of a fixed-bed skeleton catalyst, and subsequently treating the hydrogenated caprolactam with an ion exchanger. The two last-mentioned methods of treatment are extremely costly on account of the pre- and aftertreatment. Nothing is vouchsafed about how the permanganate number and the volatile bases content can be reduced in a simple and reliable manner.

It is an object of the present invention to provide a process for purifying caprolactam which is uncomplicated, which does not require the addition of acids or alkalis, a pretreatment by distillation or with ion exchangers, nor an aftertreatment with ion exchangers, and which reduces the permanganate number and the volatile bases content in a reliable manner.

We have found that this object is achieved by a process for the continuous purification of caprolactam by contacting caprolactam in an aqueous solution with hydrogen at elevated temperatures and superatmospheric pressure in the presence of a hydrogenation catalyst by passing a 75-95% strength by weight aqueous caprolactam solution together with hydrogen at 50°-95° C. and 1.5-100 bar upward through a fixed-bed supported palladium or nickel catalyst in a tubular zone while maintaining a residence time of from 10 to 100 min.

The novel process has the advantage that both the permanganate number and the volatile bases content are simultaneously reduced to a lower value. The novel process also has the advantage that it does not require expensive secondary measures, such as the addition of acids or alkalis or an additional pre- and afterpurification with activated carbon or ion exchangers. Moreover, the novel process also has the advantage that it works with concentrated aqueous solutions of caprolactam, so that there are no large quantities of water to be removed at the final distillation of the caprolactam.

The purification process will in general work with caprolactam obtained by a Beckmann rearrangement of cyclohexanoneoxime with acids, for example concentrated sulfuric acid, oleum or phosphoric acid, or by catalytic rearrangement. The starting point for the preparation of caprolactam is in general cyclohexanoneoxime prepared by oximation of cyclohexanone with hydroxylammonium salts, e.g. hydroxylammonium ammoniumsulfate, with simultaneous neutralization with ammonia, as described in DE patent U.S. Pat. No. 898,000, by oximation of cyclohexanone with hydroxylammonium salts in the presence of buffer systems, as described in GB Patent 908,859, or by oximation of cyclohexanone with hydroxylammonium salts, e.g. hydroxylammonium ammoniumsulfate, at a decreasing pH down to 0.5 or less without the additional use of neutral or buffer salts, as described in DE-A-2,508,247.

The purification process is carried out in 75-95% strength by weight aqueous solutions of caprolactam, in particular those containing from 80 to 95% by weight of caprolactam.

It is particularly advantageous to use aqueous solutions of caprolactam obtained starting from cyclohexanoneoxime prepared by oximation of cyclohexanone with hydroxylammonium ammoniumsulfate at a decreasing pH down to 0.5 without the additional use of neutral or buffer salts, by a Beckmann rearrangement of the cyclohexanoneoxime in concentrated sulfuric acid and oleum, subsequent neutralization with ammonia, removal of crude lactam, extraction of the crude lactam with an aromatic hydrocarbon such as benzene or toluene and subsequent removal of the organic solvent by distillation. The aqueous caprolactam solutions thus obtained have a caprolactam content as mentioned above.

The aqueous caprolactam solution is passed together with hydrogen upward through a fixed-bed supported palladium or nickel catalyst in a tubular zone.

Suitable supported nickel catalysts generally have a nickel content of from 5 to 80% by weight, based on metal content and carrier. Besides nickel the catalysts may also contain activating additives such as zirconium, manganese, copper or chromium, for example in amounts of from 1 to 20% by weight, based on the amount of nickel employed. The carriers used advantageously are alumina, silica gel, argillaceous earths or activated carbon. It is particularly advantageous to use magnesium silicate, aluminum phosphate, boron phosphate or alumina.

Suitable supported palladium catalysts advantageously have a palladium content of from 0.01 to 10% by weight, preferably from 0.05 to 5% by weight, in particular from 0.1 to 2% by weight, based on the sum of catalytically active metal and carrier. The carriers used advantageously are alumina, silica, titania or zirconia or mixtures thereof.

It is advantageous to use impregnated catalysts where the catalytically active metals are concentrated at the surface of the carrier. Such catalysts are prepared in a conventional manner by treating preformed carriers from the aforementioned substances in the form of pellets, spheres or cylinders with an aqueous solution of the metal salts, for example the nitrates, drying the impregnated carriers, and then calcining and reducing them with hydrogen.

The supported palladium or nickel catalysts are disposed in a fixed bed, for example as a dumped bed, in a tubular zone having a length diameter ratio of for example from 10:1 to 50:1, and the aqueous caprolactam solution and the hydrogen are passed upward in the liquid phase through the fixed bed of catalyst. After cooling and depressurization, the reaction mixture thus obtained, which consists essentially of caprolactam and water, is subjected to fractional distillation to isolate the caprolactam.

The hydrogenating treatment is carried out at from 50° to 95° C., preferably from 60° to 95° C., in particular from 70° to 90° C. The treatment is carried out by maintaining a pressure of from 1.5 to 100 bar, advantageously from 5 to 30 bar, in particular from 5 to 20 bar, and a liquid phase.

Hydrogen is used for example in amounts of from 0.0001 to 1.0 mol per mole of caprolactam, advantageously from 0.001 to 0.7 mol, in particular from 0.03 to 0.3 mol, of hydrogen per mole of caprolactam. A residence time of from 10 to 100 min, in particular from 15 to 60 min, is maintained in the treatment. Moreover, a suitable space velocity over the catalyst is from 1.0 to 6.0, in particular from 1.5 to 4, kg of caprolactam per liter of catalyst per hour.

Using the process according to the present invention it is possible to minimize the permanganate number and the volatile bases content without having to employ expensive measures, such as treatment with ion exchangers and activated carbon or other additives, such as acids or alkalis.

In what follows, the process according to the present invention is illustrated by reference to Examples, where the following abbreviations will be employed:
PMTN: permanganate titration number
PMAN: permanganate absorption number
VB: volatile bases in milliequivalents per kilogram
UV: UV number
ABS: absorb-ance
RES: residence time

EXAMPLE 1

The caprolactam used in this Example had been prepared by Beckmann rearrangement of cyclohexanoneoxime (prepared as described in DE 2,508,247) in oleum, neutralization with ammonia, extraction with benzene and evaporation of the extract, and had the following parameters:

| PMTN | PMAN | UV | ABS | VB |
|---|---|---|---|---|
| 40 | 43.6 | 77.3 | 7.1 | 0.61 |

A vertical tube reactor (diameter 16 mm, fill level 35 cm, oil-heated jacket) was packed with 70 ml (45 g) of a palladium catalyst (impregnated catalyst, 0.5% by weight of Pd finely divided on γ-alumina cylinders, d=4 mm, l=1 cm). The catalyst was activated with hydrogen over 8 hours by raising the temperature step by step from 80° to 200° C.

Thereafter an 80% strength by weight caprolactam solution in water was pumped upward through the reactor (liquid phase procedure) at a rate of from 50 to 250 ml per hour together with hydrogen (1-10 l/h) at 50 and 80° C./20 bar of hydrogen. From the top of the reactor the hydrogenation mixture passed via a cooler into a separator from where the liquid reaction product and the off-gas were discharged (length of each run 2 h). The liquid reaction product had its PMAN and VB determined. Details can be found in Table I.

TABLE I

| No. | Temp. [°C.] | Space velocity [kg/l h] | H₂/lactam [mol/mol] | RES [min] | PMAN | VB [meq/kg] |
|---|---|---|---|---|---|---|
| 0 | — | — | — | — | 43.6 | 0.61 |
| 1 | 50 | 1.7 | 0.21 | 28 | 20.0 | 0.46 |
| 2 | 80 | 1.7 | 0.21 | 28 | 10.4 | 0.53 |
| 3 | 80 | 1.7 | 0.04 | 28 | 8.4 | 0.55 |
| 4 | 80 | 1.7 | 0.42 | 28 | 7.6 | 0.44 |
| 5 | 80 | 0.6 | 0.63 | 84 | 5.0 | 0.48 |
| 6 | 80 | 2.9 | 0.13 | 17 | 12.8 | 0.50 |

COMPARATIVE EXAMPLE 1

The procedure of run 2 of Example 1 is repeated, except that a temperature of 130° C. is maintained. This gives a liquid product having a PMAN of 9.8 and a VB of 0.79. The VB value is up compared with the starting solution.

COMPARATIVE EXAMPLE 2

The caprolactam used in this Example had been prepared by Beckmann rearrangement of cyclohexanoneoxime (prepared as described in DE 2,508,247) in oleum, neutralization with ammonia, extraction with benzene and evaporation of the extract, and had the following parameters:

| PMTN | PMAN | UV | ABS | VB |
|---|---|---|---|---|
| 40 | 43.6 | 77.3 | 7.1 | 0.61 |

A vertical tube reactor (diameter 16 mm, fill level 35 cm, oil-heated jacket) was packed with 70 ml (45 g) of a palladium catalyst (impregnated catalyst, 0.5% by weight of Pd finely divided on γ-alumina cylinders, d=4 mm, l=1 cm). The catalyst was activated with hydrogen over 8 hours by raising the temperature step by step from 80° to 200° C.

Thereafter an 80% strength by weight caprolactam solution in water was pumped downward through the reactor (trickle bed phase procedure) at a rate of from 50 to 250 ml per hour together with hydrogen (1-10 l/h) at 50, 80 and 130° C./20 bar of hydrogen. From the bottom of the reactor the hydrogenation mixture passed via a cooler into a separator from where the liquid reaction product was discharged (length of each run 2 h). The liquid reaction product had its PMAN and VB determined. Table II shows the results obtained.

TABLE II

| No. | Temp. [°C.] | Space velocity [kg/l h] | H₂/lactam [mol/mol] | RES [min] | PMAN | VB [meq/kg] |
|---|---|---|---|---|---|---|
| 0 | — | — | — | — | 43.6 | 0.61 |
| 1 | 50 | 1.7 | 0.21 | 28 | 30.8 | 1.47 |
| 2 | 80 | 1.7 | 0.21 | 28 | 13.0 | 1.04 |
| 3 | 130 | 1.7 | 0.21 | 28 | 3.8 | 7.27 |
| 4 | 80 | 1.7 | 0.04 | 28 | 8.8 | 1.31 |
| 5 | 80 | 1.7 | 0.42 | 28 | 10.2 | 1.02 |
| 6 | 80 | 0.6 | 0.63 | 84 | 8.0 | 0.90 |
| 7 | 80 | 2.9 | 0.13 | 17 | 14.4 | 0.68 |

The results show that the trickle bed procedure gives distinctly worse results. Every run shows a distinct increase in the volatile bases content.

EXAMPLE 2

The caprllactam used in this Example had been prepared by Beckmann rearrangement of cyclohexanoneoxime (prepared as described in DE 2,508,247) in oleum, neutralization with ammonia, extraction with benzene and evaporation of the extract, and had the following parameters:

| PMTN | PMAN | UV | ABS | VB |
|---|---|---|---|---|
| 40 | 43.6 | 77.3 | 7.1 | 0.61 |

A vertical tube reactor (diameter 16 mm, fill level 35 cm, oil-heated jacket) was packed with 70 ml (45 g) of a palladium catalyst (impregnated catalyst, 0.5% by weight of Pd finely divided on γ-alumina cylinders, d=4 mm, l=1 cm). The catalyst was activated with hydrogen over 8 hours by raising the temperature step by step from 80° to 200° C.

Thereafter an 80% strength by weight caprolactam solution in water was pumped upward through the reactor (liquid phase procedure) with a residence time of 17 min at a rate of 250 ml per hour (=2.9 g of lactam/ml of catalyst h) together with hydrogen (5 l/h) at 80° C./20 bar of $H_2$. From the top of the reactor the reaction mixture passed via a cooler into a separator from where the liquid reaction product and the off-gas were discharged (length of run 24 h). The liquid discharge had its PMTN, PMAN, UV number, absorbance and volatile bases content determined:

| PMTN | PMAN | UV | ABS | VB |
|---|---|---|---|---|
| 16 | 11.6 | 36.9 | 3.7 | 0.43 |

The extract lactam obtained following hydrogenation thus showed distinctly improved characteristics in all parameters.

EXAMPLE 3

The caprolactam used in this Example had been prepared by Beckmann rearrangement of cyclohexanoneoxime (prepared as described in DE 2,508,247) in oleum, neutralization with ammonia, extraction with benzene and evaporation of the extract, and had the following parameters:

| PMTN | PMAN | UV | ABS | VB |
|---|---|---|---|---|
| 40 | 43.6 | 77.3 | 7.1 | 0.61 |

A vertical tube reactor (diameter 16 mm, fill level 35 cm, oil-heated jacket) was packed with 70 ml (50 g) of a supported palladium catalyst (impregnated catalyst, 0.25% by weight of Pd finely divided on γ-alumina spheres, d=2-4 mm). The catalyst was activated with hydrogen over 8 hours by raising the temperature step by step from 80° to 200° C.

Thereafter an 80% strength caprolactam solution in water was pumped upward through the reactor (liquid phase procedure) with a residence time of 28 min at a rate of 125 ml per hour (=1.4 g of lactam/ml of catalyst h) together with hydrogen (5 l/h) at 80° C./20 bar of $H_2$. From the top of the reactor the reaction mixture passed via a cooler into a separator from where the liquid reaction product and the off-gas were discharged (length of run 24 h). The liquid discharge had its PMTN, PMAN, UV number, absorbance and volatile bases content determined:

| PMTN | PMAN | UV | ABS | VB |
|---|---|---|---|---|
| 21 | 22.6 | 43.5 | 5.1 | 0.51 |

COMPARATIVE EXAMPLE 3

The caprolactam used in this Example had been prepared by Beckmann rearrangement of cyclohexanoneoxime (prepared as described in DE 2,508,247) in oleum, neutralization with ammonia, extraction with benzene and evaporation of the extract, and had the following parameters:

| PMTN | PMAN | UV | ABS | VB |
|---|---|---|---|---|
| 40 | 43.6 | 77.3 | 7.1 | 0.61 |

A vertical tube reactor (diameter 16 mm, fill level 35 cm, oil-heated jacket) was packed with 70 ml (45 g) of a palladium catalyst (impregnated catalyst, 0.5% by weight of Pd finely divided on γ-alumina cylinders, d=4 mm, l =1 cm). The catalyst was activated with hydrogen over 2 hours at 80° C.

Thereafter an 80% strength caprolactam solution in water was pumped downward through the reactor (trickle bed phase procedure) with a residence time of 28 min at a rate of 125 ml per hour (=1.4 g of lactam/ml of catalyst.h) together with hydrogen (5 l/h) at 95° C./20 bar of $H_2$. From the bottom of the reactor the reaction mixture passed via a cooler into a separator from where the liquid product and the off-gas were discharged (length of run 24 h). The liquid discharge had its PMTN, PMAN, UV number, absorbance and volatile bases content determined:

| PMTN | PMAN | UV | ABS | VB |
|---|---|---|---|---|
| 18 | 15.6 | 35.7 | 3.5 | 1.26 |

The volatile bases content is above the starting value.

EXAMPLE 4

The caprolactam used in this Example had been prepared by a Beckmann rearrangement of cyclohexanoneoxime (prepared as described in DE 2,508,247) in oleum, neutralization with ammonia, extraction with benzene and evaporation of the extract, and had the following parameters:

| PMTN | PMAN | VB |
|---|---|---|
| 46 | 30.1 | 0.76 |

A vertical tube reactor (diameter 16 mm, fill level 35 cm, oil-heated jacket) was packed with 70 ml (70 g) of a nickel catalyst (56% by weight of NiO finely divided on magnesium silicate pellets, d =5 mm). The catalyst was activated with hydrogen over 8 hours by raising the temperature step by step from 80° to 200° C.

Thereafter an 80% strength caprolactam solution in water was pumped upward through the reactor (liquid phase procedure) at a rate of from 50 to 250 ml per hour together with hydrogen (1-10 l/h) at 50° and 80° C./20 bar of hydrogen. From the top of the reactor the hydrogenation mixture passed via a cooler into a separator from where the liquid reaction product and the off-gas were discharged (length of each run 2 h). The liquid reaction product had its PMAN determined for each run.

Table III gives an overview of the conditions and results obtained.

TABLE III

| No. | Temp. [°C.] | Space velocity [kg/l h] | H$_2$/lactam [mol/mol] | RES [min] | PMAN |
|---|---|---|---|---|---|
| 0 | — | — | — | — | 30.1 |
| 1 | 50 | 1.7 | 0.21 | 28 | 19.0 |
| 2 | 80 | 1.7 | 0.21 | 28 | 12.8 |
| 3 | 80 | 1.7 | 0.04 | 28 | 21.8 |
| 4 | 80 | 1.7 | 0.42 | 28 | 19.0 |
| 5 | 80 | 0.6 | 0.63 | 84 | 11.4 |
| 6 | 80 | 2.9 | 0.13 | 17 | 21.0 |

COMPARATIVE EXAMPLE 4

The caprolactam used in this Example had been prepared by a Beckmann rearrangement of cyclohexanoneoxime (prepared as described in DE 2,508,247) in oleum, neutralization with ammonia, extraction with benzene and evaporation of the extract, and had the following parameters:

| PMTN | PMAN | VB |
|---|---|---|
| 46 | 30.1 | 0.76 |

A vertical tube reactor (diameter 16 mm, fill level 35 cm, oil-heated jacket) was packed with 70 ml (70 g) of a nickel catalyst (56% by weight of NiO finely divided on magnesium silicate pellets, d = 5 mm). The catalyst was activated with hydrogen over 8 hours by raising the temperature step by step from 80° to 200° C.

Thereafter an 80% strength caprolactam solution in water was pumped downward through the reactor (trickle bed procedure) at a rate of from 50 to 250 ml per hour together with hydrogen (1–10 l/h) at from 50° to 130° C./20 bar of hydrogen. From the bottom of the reactor the hydrogenation mixture passed via a cooler into a separator from where the liquid reaction product and the off-gas were discharged(length of each run 2 h). The liquid reaction product had its PMAN determined for each run.

Table IV gives an overview of the results obtained:

TABLE IV

| No. | Temp. [°C.] | Space velocity [kg/l h] | H$_2$/lactam [mol/mol] | RES [min] | PMAN |
|---|---|---|---|---|---|
| 0 | — | — | — | — | 30.1 |
| 1 | 50 | 1.7 | 0.21 | 28 | 23.4 |
| 2 | 80 | 1.7 | 0.21 | 28 | 19.8 |
| 3 | 130 | 1.7 | 0.21 | 28 | 14.0 |
| 4 | 80 | 1.7 | 0.04 | 28 | 29.4 |
| 5 | 80 | 1.7 | 0.42 | 28 | 19.6 |
| 6 | 80 | 0.6 | 0.63 | 84 | 15.2 |
| 7 | 80 | 2.9 | 0.13 | 17 | 31.2 |

The results testify that under the same conditions as in Example 4 the trickle bed procedure gives distinctly worse results. The improvement in PMAN does not attain the level achieved by the liquid phase procedure.

COMPARATIVE EXAMPLE 5

SUSPENSION CATALYSTS

The caprolactam used in this Example had been prepared by Beckman rearrangement of cyclohexanoneoxime (prepared as described in DE Pat. No. 2,508,247) in oleum, neutralization with ammonia, extraction with benzene and evaporation of the extract, and had the following parameters:

| PMTN | UV | ABS | VB |
|---|---|---|---|
| 29 | 55.7 | 4.9 | 0.34 |

200 g of a 95% strength caprolactam solution in water and the amount of catalyst specified in the table were introduced into a magnetically stirred 400 ml glass autoclave, heated to the reaction temperature and then stirred under 10 bar of H$_2$ for the stated period. At the end of each run, the PMTN and VB values were determined. Details are shown in Table V.

TABLE V

| No. | Catalyst | Temp. [°C.] | Time [min] | PMTN | VB [meq/kg] |
|---|---|---|---|---|---|
| 0 | — | — | — | 29 | 0.34 |
| 1 | 1600 mg of Raney nickel | 80 | 30 | 6.3 | 0.38 |
| 2 | 4000 mg of 56% NiO/MgSiO$_3$ | 95 | 60 | 10 | 0.38 |
| 3 | 1600 mg of 10% Pd/carbon | 80 | 30 | 5.8 | 0.40 |
| 4 | 1600 mg of 1.3% Ru/Al$_2$O$_3$ | 80 | 60 | 8.5 | 0.60 |

The results show that a suspension hydrogenation gives distinctly worse results. It is true that the hydrogenation product mixtures show a distinct improvement in PMTN, but only at the expense of an increase in the volatile bases content.

The parameters were determined as follows:

Permanganate titration number (PMTN)

The resistance of caprolactam to potassium permanganate is determined titrimetrically. The permanganate titration number (PMTN) is the consumption of 0.1 N potassium permanganate solution in ml per 1 kg of caprolactam found on titration of a solution in sulfuric acid.

Permanganate absorption number (PMAN)

The resistance of caprolactam to potassium permanganate is determined photometrically. To this end, equal amounts of a 0.01 N potassium permanganate solution are added to a 1% (m/m) aqueous caprolactam solution and to a blank (distilled water). After 10 minutes the absorbances E at 420 nm of the caprolactam sample and the blank are compared. The permanganate absorption number is calculated from the absorbance measured at 420 nm × 100.

Volatile bases (VB)

Determination in a Parnas apparatus; see also ISO method 8661 ("Caprolactam for industrial use—Determination of volatile bases content")

On distillation in an alkaline medium the volatile bases evolve from the sample (Kjeldahl apparatus), are trapped in 0.02 N hydrochloric acid and determined by titration with 0.02 N sodium hydroxide solution.

$$VB = \frac{(B - A) \times 0.02}{20} \times 1000$$

A = consumption of 0.02 N sodium hydroxid solution

B = consumption of 0.02 N sodium hydroxide solution for blank sample

UV number (UV)

The absorbances of a 50% (m/m) aqueous caprolactam solution at 270, 280, 290, 300, 310, 320, 330, 340, 350 and 360 nm are determined in a 10 cm cell. The total of the absorbances is multiplied by 2 and the product is the UV number for 100 percent pure caprolactam.

Absorbance (ABS)

The absorbance A of a 50% (m/m) aqueous caprolactam solution is measured at a wavelength of 290 nm and related to a path length l = 1 cm.

We claim:

1. A process for the continuous purification of caprolactam by passing a 75-95% strength by weight aqueous caprolactam solution together with hydrogen at 50°-95° C. and 1.5-100 bar upward through a fixed-bed supported palladium or nickel catalyst in a tubular zone while maintaining a residence time of from 10 to 100 min.

2. A process as claimed in claim 1, wherein a space velocity is maintained over the catalyst of from 1 to 6 kg of caprolactam per liter of catalyst per hour.

3. A process as claimed in claim 1, wherein a residence time of from 15 to 60 min is maintained.

4. A process as claimed in claim 1, wherein a pressure of from 5 to 20 bar is maintained.

5. A process as claimed in claim 1, wherein a temperature of from 70° to 90° C. is maintained.

6. A process as claimed in claim 1, wherein a 0.1-2% strength by weight supported palladium catalyst is used.

7. A process as claimed in claim 1, wherein a 5-80% strength by weight supported nickel catalyst is used.

* * * * *